United States Patent [19]

Sweet

[11] Patent Number: 4,583,393

[45] Date of Patent: Apr. 22, 1986

[54] ULTRASONIC DENSITY METER WITH DAMPING

[75] Inventor: Edmund G. F. Sweet, Burlington, Canada

[73] Assignee: Ontario Research Foundation, Mississauga, Canada

[21] Appl. No.: 591,110

[22] Filed: Mar. 20, 1984

[51] Int. Cl.⁴ .............................................. G01N 9/00
[52] U.S. Cl. ...................... 73/32 A; 73/438
[58] Field of Search .................... 73/32 R, 32 A, 438, 73/290 V

[56] References Cited

U.S. PATENT DOCUMENTS

| | | | |
|---|---|---|---|
| 1,602,444 | 10/1926 | Naiman | 73/32 R |
| 2,279,254 | 4/1942 | Irwin | 73/438 |
| 2,775,748 | 12/1956 | Rod et al. | 73/290 V |
| 3,190,126 | 6/1965 | Wright | 73/438 |
| 3,553,636 | 1/1971 | Baird | 73/290 V |

Primary Examiner—Stewart J. Levy
Assistant Examiner—John E. Chapman, Jr.
Attorney, Agent, or Firm—Sim & McBurney

[57] ABSTRACT

A density meter includes a main body having a vertically elongated chamber to contain a test fluid. A passageway in the main body connects to the chamber near its bottom end. The passageway spans at least a bottom portion of the chamber and leads to the exterior of the main body. The chamber has in its lower end a liquid which is immiscible with and denser than the test fluid, the liquid also occupying at least part of the passageway. Access means are provided for admitting the test fluid to the chamber and evacuating it therefrom. Measuring means are provided for determining the location of the top surface of the liquid. The measuring means to determine the location of the liquid top is preferably ultrasonic.

17 Claims, 1 Drawing Figure

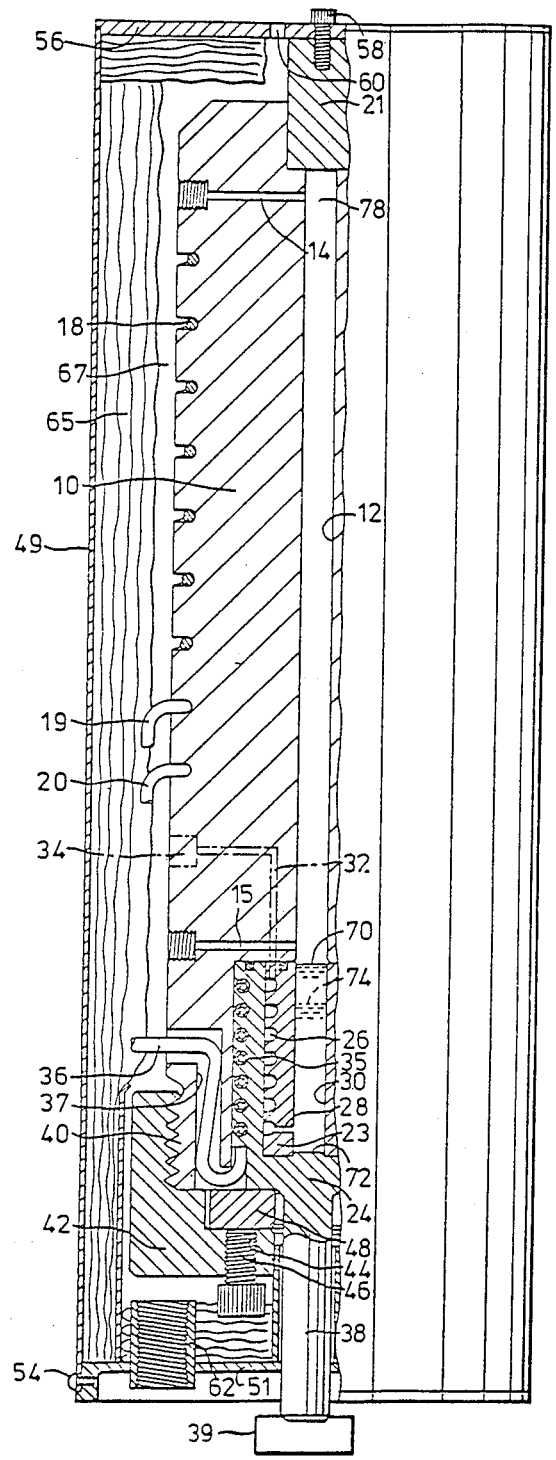

ULTRASONIC DENSITY METER WITH DAMPING

This invention relates generally to density meters, and deals particularly with a density meter which is adapted for determining accurately the density of a test fluid such as drilling mud. In a preferred embodiment, the density determination can be made at elevated temperatures and pressures.

BACKGROUND OF THIS INVENTION

While the density meter to be disclosed herein is capable of determining the density of any test fluid, the particular embodiment to be described has been developed for the purpose of determining accurately the density of a drilling fluid utilized in well-drilling operations. This drilling fluid, sometimes called "drilling mud", has a number of basic purposes in the drilling of a well. One purpose is to cool and lubricate the bit and the string. Another is to carry up to the surface the bore-hole material which is produced as a result of the drilling operation. A third purpose is to deposit a tough and low-permeability filter cake against the sides of the bore-hole and thus reduce the invasion of the fluid phase into the formation and control the loss of the fluid phase down hole. A fourth is to overbalance formation pore-pressures with sufficient hydrostatic head in order to control well flowing. A fifth is for control of corrosion of the drill string and bit, and a sixth is to buoyantly support the drill string.

Due to geothermal heat in the surrounding formations, the temperature of the drilling fluid can rise as high as 600° F. or more. The pressure of the drilling fluid is a function of depth and density, and for very deep wells, the pressure placed upon the drilling fluid at the bottom of the fluid can be as high as 20,000 psi or more.

At least some of the performance characteristics of a given drilling fluid are influenced by or depend upon the density of the fluid. An example is the purpose of buoyantly supporting the drill string. Also, the total pressure developed in the fluid, which is a factor in over balancing formation pore pressures, is obviously dependent upon the density.

It is therefore of considerable benefit to know accurately the density of a given drilling fluid, preferably at elevated temperatures and pressures.

The prior art contains the following patents of interest:

U.S. Pat. No. 4,117,716, issued Oct. 3, 1978 to Simon
U.S. Pat. No. 3,553,636, issued Jan. 5, 1971 to Baird
U.S. Pat. No. 3,690,184, issued Sept. 12, 1972 to Chadenson
U.S. Pat. No. 3,368,393, issued Feb. 13, 1968 to Wilson et al
U.S. Pat. No. 2,279,254, issued Apr. 7, 1942 to Irwin
U.S. Pat. No. 3,782,199, issued Jan. 1, 1974 to Bell
U.S. Pat. No. 3,008,332, issued Nov. 14, 1961 to Charbonnier et al.

Because none of the prior art patents listed above proposes to measure the density of a test fluid under conditions of elevated temperature and pressure, they do not encounter and do not have to solve the problems associated with that determination. These problems will be more clearly apparent during the subsequent detailed description of the present invention.

GENERAL DESCRIPTION OF THIS INVENTION

The basic principle of operation of the density meter to be described herein is that of placing a column of the test fluid above a column of what may be termed calibration liquid, the latter being heavier than and immiscible with the test fluid, and located in the equivalent of a manometer-like U-tube. Because the calibration liquid is immiscible with the test fluid, an interface between the two is established, and the vertical position of the this interface, and changes in that position, are used to determine the density of the test fluid.

The apparatus to be described herein is capable of being utilized in a "flow-through" mode, in which the test fluid cycles continuously through the column above the calibration liquid. Because it is the nature of most pumps to superimpose a pressure pulse on the fluid or liquid being pumped, there will naturally arise a tendency for the interface between the calibration liquid and the test fluid to oscillate. Accordingly, the present invention seeks to damp such oscillation, by providing particular configurational characteristics for the compartment occupied by the calibration liquid.

Furthermore, since this invention proposes to have the capability of measuring the density of a test fluid at elevated temperatures and pressures, the actual column of the test fluid must be contained and protected within a body of substantial mass, such that visual determination of levels is not practical. Accordingly, this invention provides an ultrasonic means of determining the vertical position of only a single level, namely the top surface of the calibration liquid which is the same as the interface between the calibration liquid and the test fluid, such that a determination of the vertical height of that level before and after the test fluid has been admitted will permit an accurate calculation of the density of the test fluid. This is made possible by the fact that the top surface of the test fluid is always known, due to the particular design employed. Therefore, the top surface of the test fluid does not need to be determined visually or by any other means.

More particularly, this invention provides a density meter comprising:
  a main body,
  a vertically elongated chamber in said main body adapted to contain a test fluid, the chamber having a bottom end and a top end,
  a passageway in said main body connecting to the chamber adjacent the bottom end of the chamber, the passageway vertically spanning at least a bottom portion of the chamber and leading to the exterior of said main body,
  the chamber containing in its lower end a liquid which is immiscible with and denser than said test fluid, the liquid also occupying at least part of said passageway,
  access means communicating with the chamber at two longitudinally spaced apart locations therealong, whereby test fluid may be admitted to and evacuated from the chamber,
  and measuring means for determining the location of the top surface of the liquid in the chamber, said measuring means including an ultrasonic device at the bottom of the chamber adapted to generate an ultrasound signal in the said liquid and to detect the return of the echo of said signal from the said top surface of the liquid in the chamber, the access means including an entry near the top of the chamber and an exit near the bottom of the chamber.

This invention further provides a method of determining the density of a test fluid, comprising the steps:

providing a main body having a vertically elongated chamber adapted to contain the test fluid, the chamber having a bottom end and a top end, a passageway in said main body connecting to the chamber adjacent the bottom end of the chamber, the passageway vertically spanning at least a bottom portion of the chamber and leading to the exterior of said main body, placing in the lower end of the chamber and in at least part of the passageway a liquid which is immiscible with and denser than said test fluid, measuring the vertical position of the top surface of the liquid by generating an ultrasound signal in the liquid at the bottom of the chamber and detecting the return of the echo of said signal from the top surface of the liquid in the chamber, admitting the test fluid to the chamber through an access port near the top end thereof until it fills the chamber above the liquid to the level of the access port, thereby expelling some of the liquid into said passageway and lowering the top surface of the liquid in the chamber, measuring the new vertical position of the top surface of the liquid by again generating an ultrasound signal in the liquid at the bottom of the chamber and detecting the return of the echo of said signal from the top surface of the liquid in the chamber, and calculating the density of the test fluid on the basis of the depression of the top surface of the liquid by the weight of the test fluid, the height of the test fluid above the liquid, and the geometry of the passageway.

This invention further provides a method of determining the density of a test fluid, comprising the steps:

providing a main body having a vertically elongated chamber adapted to contain the test fluid, the chamber having a bottom end and a top end, a passageway in said main body connecting to the chamber adjacent the bottom end of the chamber, the passageway vertically spanning at least a bottom portion of the chamber and leading to the exterior of said main body, placing in the lower end of the chamber and in at least part of the passageway a liquid which is immiscible with and denser than said test fluid, measuring the vertical position of the top surface of the liquid by generating an ultrasound signal in the liquid at the bottom of the chamber and detecting the return of the echo of said signal from the top surface of the liquid in the chamber, continuously circulating the test fluid through the chamber between an inlet and an outlet which are spaced apart longitudinally, the uppermost of the inlet and outlet establishing the top of the column of test fluid, continuously measuring the vertical position of the top surface of the liquid by again generating an ultrasound signal in the liquid at the bottom of the chamber and detecting the return of the echo of said signal from the top surface of the liquid in the chamber, and calculating from time to time the density of the test fluid on the basis of the depression of the top surface of the liquid by the weight of the test fluid, the height of the test fluid above the liquid, and the geometry of the passageway.

GENERAL DESCRIPTION OF THE DRAWING

In the accompanying drawing, the single FIGURE is a part elevation and part axial sectional view through a density meter constructed in accordance with this invention.

DETAILED DESCRIPTION OF THE DRAWING

With reference to the drawing, a main body 10 is of generally cylindrical configuration and is machined preferably from high-strength steel. The main body 10 has an axial, central bore 12 constituting an elongated chamber in the main body 10 adapted to contain a test fluid, and lateral access passages 14 and 15 are drilled through the main body 10 to communicate with the top end and bottom end, respectively, of the chamber constituted by the central bore 12. A conventional heating element 18 of the Cal-rod type has two leads 19 and 20, and is wrapped around a helical groove in the main body 10, as illustrated. At the upper end of the bore 12, a short expanded portion of the bore is closed and blocked by a solid cylindrical member 21, located above the level of the access port 14.

At the bottom end of the main body 10 are two nested members 23 and 24. The member 23 is a hollow cylinder having an external spiral groove 26 which has access at its lower end through a port 28 to an inner bore 30 of the member 23, the bore 30 being in communication with and aligned with the bore 12. In the embodiment shown, the bore 30 and the bore 12 have the same diameter. At its top, the spiral groove 26 communicates along a passage 32, drilled through the main body 10, with a nitrogen admission port 34.

The member 24 fits closely around the member 23, thus closing the outside of the spiral groove 26, so that the latter defines a spiral passageway which can contain liquid. The member 24 has a cylindrical outer surface into which is cut a further spiral groove 35, and into this spiral groove 35 is wrapped a heating element 36 with leads exiting through a passage 37 in the main body 10.

The member 24 is essentially cup-shaped and includes an integral, coaxial downward extension 38, adapted to be coupled to a device 39 for generating an ultrasonic signal travelling axially upwardly. The use of this ultrasonic signal in relation to the fluids in the apparatus will be described subsequently.

The main body 10 is externally threaded at its lower end 40, the threads being adapted to engage a nut 42 which has a plurality of threaded bores 44 for receiving a plurality of lock bolts 46 adapted to bear upwardly against an annular insert 48 which in turn bears against the member 24.

An external shell is provided for the main body 10, the shell comprising an outer cylindrical wall 49, a lower annular wall 51 secured to the outer wall 49 by bolts 54, and a top wall 56 welded to the top of the outer wall 49. A machine bolt 58 secures the top wall 56 to the solid cylindrical member 21. A plurality of air-escape holes 60 are provided adjacently around the bolt 58.

In the bottom wall 51 is provided a threaded tube 62 adapted to receive a coupling connected to a source of air under pressure.

As can be seen in the figure, the entire inside surface of the shell constituted by the walls 49, 51 and 56 is lined with insulating material 65, leaving a space 67 between the insulating material 65 and the main body 10.

In operation, the apparatus described above and shown in the drawing first receives a liquid which is denser than and immiscible with the test fluid of which the density is to be measured. In a preferred embodiment, this liquid is woods metal, and because woods metal is solid at room temperatures, at least the lower end of the apparatus must be heated by means of the heating element 36 prior to the admission of the woods metal. Furthermore, the woods metal itself must be raised above its melting point for admission.

The woods metal is admitted to the central chamber constituted by the bore 12, either through the passage 14 or through the passage 15, and it accumulates until the level reaches that shown at 70 in the figure, or thereabouts. Because of the communication provided by the port 28, the woods metal also flows into and fills the spiral groove 26, up to the same level as that shown at 70 in the figure.

The next step in the method is to utilize an ultrasonic device coupled to the extension 38 to determine the vertical location of the top surface 70 of the woods metal. This is done by a well known echo technique, in which the ultrasonic device generates a pulse in the woods metal beginning from the location 72, and then detects the arrival of the echo of that pulse at the same location 72 after reflection from the surface 70 (which is a liquid/gas interface). The technology for accomplishing this measurement is well known, and need not be described in detail here.

The next step is to admit the test fluid, for example drilling mud, to the bore 12 through the passage 14, while the passage 15 is closed or blocked. The drilling mud is admitted until it rises to and backs up through the passage 14. This will establish at the line 78 an accurate position for the top of the test fluid (drilling mud). Alternatively, the test fluid could be admitted through the passage 15 while the passage 14 remains open, until the fluid were seen to spill out of the passage 14.

During the admission of the test fluid into the bore 12, the interface 70 between the test fluid and the woods metal gradually is depressed by the weight of the column of test fluid, and may end at a level shown by way of example at the numeral 74 in the figure. This will be accompanied by a rise in the level of woods metal into the passage 32, such rise depending upon the geometry of that passage. In a preferred embodiment, a given drop in the level of the woods metal in the inner bore 30 is accompanied by an equivalent rise in the level of the woods metal in the passage 32, which requires the bore 30 and the passage 32 to have the same cross-section. The drawing illustrates at 32 only one of a possible plurality of such passages, which would have the same aggregate cross-sectional area as the bore 30.

In order to provide an example, let us assume that the rise of the level of the woods metal in the passage 32 is exactly the same as the drop in the level of the woods metal in the bore 30 under the weight of the column of test fluid in the bore 12. Since the level of the top of the test fluid is accurately determined by the position of the passage 14, an accurate determination of the density of the test fluid is now possible, utilizing the known density of the woods metal and the measured drop of the interface 70.

If the initial vertical distance between the level 70 (the top of the woods metal with no test fluid above it) and the level 78 is $H_{tf}$, and if the depression of the column of woods metal due to the weight of the column of test fluid is $\Delta H$, then the density of the test fluid ($\rho_{tf}$) can be expressed in terms of the density of the woods metal ($\rho_{wm}$) and will conform to the following equation:

$$2\Delta H \cdot \rho_{wm} = (H_{tf} + \Delta H)\rho_{tf}$$

Therefore $\rho_{tf} = (1310\Delta H)/(12+\Delta H)$ pounds per foot$^3$.

This is based on a density of 655 pounds per cubic foot for woods metal, and $H_{tf} = 12$ inches.

In order to determine the density of the test fluid under conditions of elevated temperature, the heating element 18 is energized, thus raising the temperature of the main body 10 and of the test fluid in the bore 12. In order to determine the density under conditions of elevated pressure, nitrogen or another gas which does not react with the woods metal or the test fluid may be admitted to the passage (or passages) 32 and the passage 14 while the passage 15 is closed. The nitrogen being admitted to these two passages must come from the same source so that the pressures are equalized and will not disturb the reading of levels.

Upon completion of the test, the test fluid may be withdrawn from the bore 12 through the passage 15 after the pressure has been reduced to atmospheric.

Subsequent to the testing procedure it may be desired to quickly cool the main body 10. This is accomplished by admitting pressurized air through the sleeve 62, so that it will be flushed alongside the main body 10, and exit through the ports 60.

During the test, and while heating the main body 10 by means of the electrical heater 18, the insulation 65 serves to reduce heat loss and improve the efficiency.

The apparatus described hereinabove is also adapted for continuous monitoring of the density of a test fluid such as drilling mud. In this mode of operation, the test fluid would be pumped through the bore 12, circulating either from the passage 14 to passage 15, or in the reverse direction. In particular, by pumping the test fluid in at the passage 15 and allowing it to spill out at the passage 14, the latter establishes accurately the top of the column of test fluid. This is identified by the numeral 78 in the FIGURE.

It is especially during use of this apparatus in the continuous monitoring mode that the configurational characteristics at the lower end become important. It will be appreciated that many circulating pumps superimpose pressure pulses on the liquids which they are moving, and it will therefore be understood that, when such a circulating pump is pumping test fluid continously through the port 12, the pressure pulse will tend to cause an oscillation in the vertical position of the interface 70. The ultrasonic measuring device is quite capable of making a very fine measurement of the vertical position of the interface 70 at any given moment, and the typical oscillation in the location of that interface due to the pump may be substantially greater than the resolution that can be obtained with the ultrasonic device, unless some means is provided for resisting or damping such oscillation.

The construction of this density meter incorporates several features, all of which tend in the direction of resisting or damping oscillations in the interface 70 due to pumping. Firstly, the provision of the restricted port 28 contributes a resistive damping of any oscillations in the vertical position of the interface 70. Secondly, the provision of the relatively long helical passageway 26, all of it filled with woods metal, provides a very substantial mass of the woods metal, thus contributing inertial damping of any oscillations which might arise in the vertical position of the interface 70. Finally, the helical passageway has a relatively high ratio of surface to contained volume, thereby contributing a frictional damping of any oscillations in the vertical position of the interface 70.

These structural characteristics act together to limit oscillations, but would also have some damping effect if acting in isolation or in pairs.

While one embodiment of this invention has been illustrated in the appended drawing and described hereinabove, it will be apparent to those skilled in the art that changes and modifications may be made therein without departing from the essence of this invention, as set forth in the attached claims.

The embodiments of the invention in which an exclusive property or privilege is claimed are defined as follows:

1. A density meter comprising:
    a main body,
    a vertically elongated chamber in said main body adapted to contain a test fluid, the chamber having a bottom end and a top end,
    a passageway in said main body connecting to the chamber adjacent the bottom end of the chamber, the passageway vertically spanning at least a bottom portion of the chamber and leading to the exterior of said main body,
    the chamber containing in its lower end a liquid which is immiscible with and denser than said test fluid, the liquid also occupying at least part of said passageway,
    access means communicating with the chamber at two longitudinally spaced apart locations therealong, whereby test fluid may be admitted to and evacuated from the chamber,
    and measuring means for determining the location of the top surface of the liquid in the chamber, said measuring means including an ultrasonic device at the bottom of the chamber adapted to generate an ultrasound signal in the said liquid and to detect the return of the echo of said signal from the said top surface of the liquid in the chamber, the access means including an entry near the top of the chamber and an exit near the bottom of the chamber.

2. The density meter claimed in claim 1, in which the least part of said passageway has the configuration of a helix encircling said bottom portion of the chamber.

3. The density meter claimed in claim 1, in which said liquid is woods metal, the density meter further comprising heating means for heating the woods metal above its melting point.

4. The density meter claimed in claim 3, in which said heating means includes a helical electrical heating element in said main body surrounding said passageway.

5. The density meter claimed in claim 4, in which said passageway is configured as a helix encircling the chamber, the passageway and the helical heating element being all substantially coaxial.

6. The density meter claimed in claim 1, in which one location is adjacently above the top of said liquid, the other said location being above said one location.

7. The density meter claimed in claim 1, in which the main body is substantially an upright cylinder having a coaxial bore which at least in part defines said chamber, the main body being enwrapped with further heating means adapted to raise the temperature of the main body and the test fluid in said chamber, and in which means to pressurize the chamber is provided.

8. The density meter claimed in claim 1, in which the main body is substantially an upright cylinder having a coaxial bore which at least in part defines said chamber, the main body being enwrapped with further heating means adapted to raise the temperature of the main body and the test fluid in said chamber, and in which means to pressurize the chamber is provided.

9. The density meter claimed in claim 8, in which the main body is enclosed within a shell having a layer of insulating material surrounding but spaced from said main body, and entry and exit ports by which cooling air can be circulated in the space between the material and the main body.

10. The density meter claimed in claim 1, in which the passageway includes a restricted region of relatively small section, thereby to resistively damp oscillations which might arise in the vertical position of the top surface of the liquid due to the fluid being pumped through the chamber.

11. The density meter claimed in claim 1, in which the passageway is relatively long, whereby it contains a substantial mass of said liquid, thereby to inertially damp oscillations which might arise in the vertical position of the top surface of the liquid due to the fluid being pumped through the chamber.

12. The density meter claimed in claim 1, in which the passageway has a relatively high ratio of internal surface to internal contained volume, thereby to frictionally damp oscillations which might arise in the vertical position of the top surface of the liquid due to the fluid being pumped through the chamber.

13. A method of determining the density of a test fluid, comprising the steps:
    providing a main body having a vertically elongated chamber adapted to contain the test fluid, the chamber having a bottom end and a top end, a passageway in said main body connecting to the chamber adjacent the bottom end of the chamber, the passageway vertically spanning at least a bottom portion of the chamber and leading to the exterior of said main body,
    placing in the lower end of the chamber and in at least part of the passageway a liquid which is immiscible with and denser than said test fluid,
    measuring the vertical position of the top surface of the liquid by generating an ultrasound signal in the liquid at the bottom of the chamber and detecting the return of the echo of said signal from the top surface of the liquid in the chamber,
    admitting the test fluid to the chamber through an access port near the top end thereof until it fills the chamber above the liquid to the level of the access port, thereby expelling some of the liquid into said passageway and lowering the top surface of the liquid in the chamber,
    measuring the new vertical position of the top surface of the liquid by again generating an ultrasound signal in the liquid at the bottom of the chamber and detecting the return of the echo of said signal from the top surface of the liquid in the chamber,
    and calculating the density of the test fluid on the basis of the depression of the top surface of the liquid by the weight of the test fluid, the height of the test fluid above the liquid, and the geometry of the passageway.

14. The method claimed in claim 13, in which the passageway has the configuration of a helix encircling the bottom portion of the chamber.

15. The method claimed in claim 13, further including the steps of heating the test fluid by conduction through said main body, and pressurizing the test fluid by means of pressurized gas.

16. A method of determining the density of a test fluid, comprising the steps:

providing a main body having a vertically elongated chamber adapted to contain the test fluid, the chamber having a bottom end and a top end, a passageway in said main body connecting to the chamber adjacent the bottom end of the chamber, the passageway vertically spanning at least a bottom portion of the chamber and leading to the exterior of said main body, placing in the lower end of the chamber and in at least part of the passageway a liquid which is immiscible with and denser than said test fluid, measuring the vertical position of the top surface of the liquid by generating an ultrasound signal in the liquid at the bottom of the chamber and detecting the return of the echo of said signal from the top surface of the liquid in the chamber, continuously circulating the test fluid through the chamber between an inlet and an outlet which are spaced apart longitudinally, the uppermost of the inlet and outlet establishing the top of the column of test fluid, continuously measuring the vertical position of the top surface of the liquid by again generating an ultrasound signal in the liquid at the bottom of the chamber and detecting the return of the echo of said signal from the top surface of the liquid in the chamber, and calculating from time to time the density of the test fluid on the basis of the depression of the top surface of the liquid by the weight of the test fluid, the height of the test fluid above the liquid, and the geometry of the passageway.

17. The method claimed in claim 16, further including the steps of heating the test fluid by conduction through the main body, and pressurizing the test fluid by means of pressurized gas.

* * * * *